United States Patent [19]

Murphy

[11] 4,175,019
[45] Nov. 20, 1979

[54] HEATED SOLID ELECTROLYTE OXYGEN SENSOR

[75] Inventor: Michael P. Murphy, Flint, Mich.

[73] Assignee: General Motors Corporation, Detroit, Mich.

[21] Appl. No.: 892,644

[22] Filed: Apr. 3, 1978

[51] Int. Cl.² ............................................. G01N 27/46
[52] U.S. Cl. ................................. 204/195 S; 338/271
[58] Field of Search .............................. 204/1 S, 195 S

[56] References Cited

U.S. PATENT DOCUMENTS

| | | | |
|---|---|---|---|
| 2,030,937 | 2/1936 | Reichmann | 123/145 A |
| 2,898,571 | 8/1959 | Moule et al. | 338/238 |
| 3,252,122 | 5/1966 | Baxter | 338/271 |
| 3,546,086 | 12/1970 | Sayles | 204/195 S |
| 3,616,274 | 10/1971 | Eddy | 204/1 S |
| 3,815,560 | 6/1974 | Wahl et al. | 123/117 R |
| 3,844,920 | 10/1974 | Burgett et al. | 204/195 S |
| 3,915,828 | 10/1975 | Cleary et al. | 204/195 S |
| 3,928,161 | 12/1975 | McIntyre et al. | 204/195 S |
| 3,999,947 | 12/1976 | Mihara et al. | 23/254 E |

FOREIGN PATENT DOCUMENTS 2131365 11/1972 France .
1367389 9/1974 United Kingdom .

Primary Examiner—T. Tung
Attorney, Agent, or Firm—Robert J. Wallace

[57] ABSTRACT

A readily manufacturable heated solid electrolyte oxygen sensor. The sensor includes a heater supported on a tubular reference electrode terminal in desired position relative to a solid electrolyte member within a cylindrical housing. The heater and terminal are constructed as a subassembly readily assemblable in concentric relationship with the solid electrolyte member and the housing.

6 Claims, 11 Drawing Figures

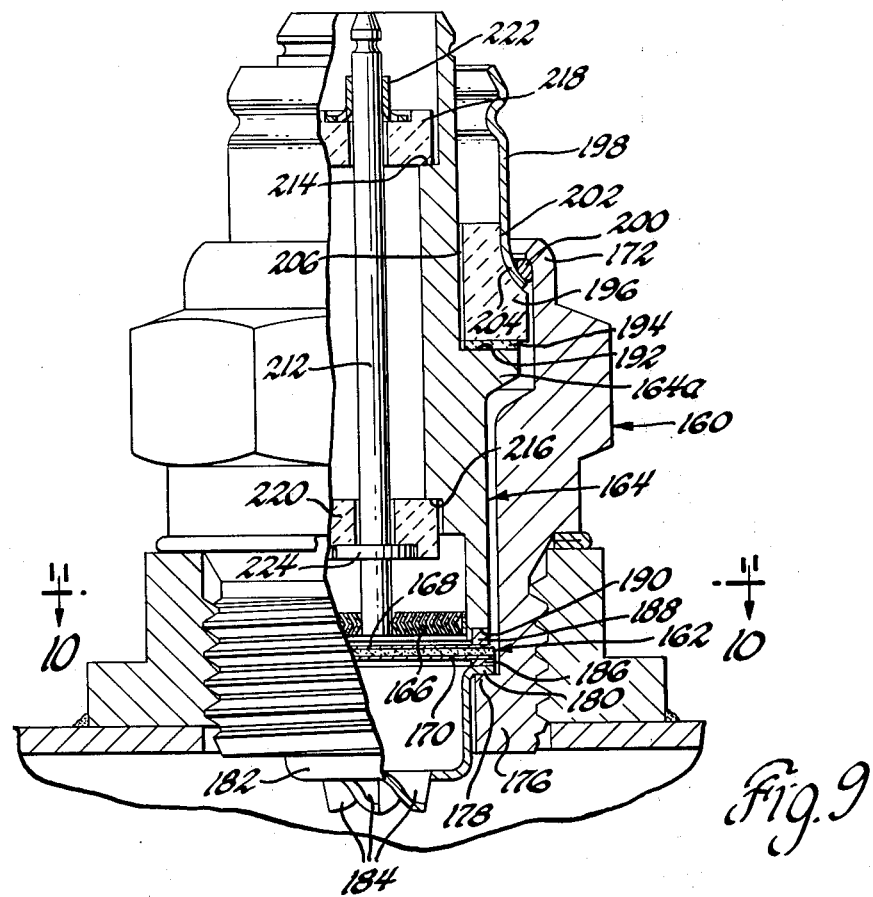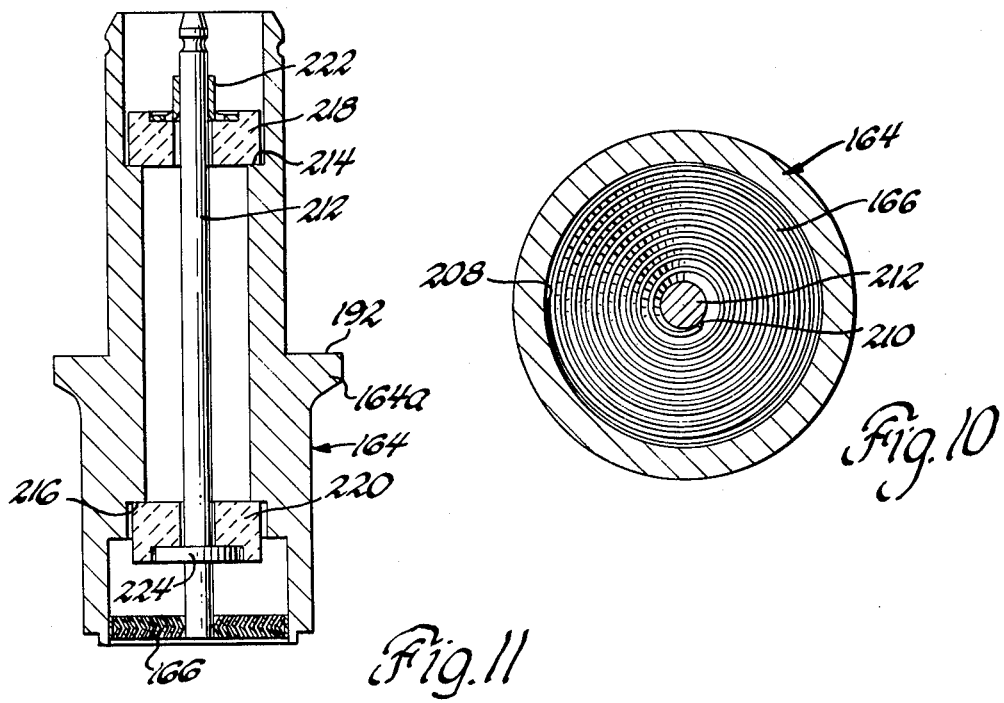

HEATED SOLID ELECTROLYTE OXYGEN SENSOR

BACKGROUND OF THE INVENTION

This invention relates to a heated galvanic-type solid electrolyte oxygen sensor, and more particularly to an improved and readily assemblable construction of such a sensor.

Solid electrolyte galvanic oxygen sensors essentially include an oxygen-ion-conductive ceramic body with porous electrodes on opposite faces of the body. One electrode is exposed to a reference source of oxygen. The other electrode is exposed to a source whose oxygen content is to be measured. A difference in oxygen partial pressure at the electrodes results in a corresponding electrode potential difference, providing a sensor output voltage.

The output voltage of such sensors can be used to measure oxygen or unburned combustibles in combustion gases produced by an internal combustion engine. This voltage can be used in monitoring and controlling the combustion process, as disclosed in U.S. Pat. Nos. 3,616,274 Eddy, 3,844,920 Burgett et al and U.S. Ser. No. 787,900 Howarth, filed Apr. 15, 1977, now U.S. Pat. No. 4,129,099.

The solid electrolyte of such a sensor must be heated to an elevated temperature to obtain an appreciable output voltage. Also, sensor output voltage varies directly with changes in temperature, especially at lower operating temperatures. Combustion gases can be used to heat the sensor to operating temperatures but such gases vary widely in temperature, particularly when from an internal combustion engine. The aforementioned U.S. Pat. No. 3,616,724 Eddy discloses sensor temperature compensating means that includes a surrounding resistance heater. U.S. Pat. No. 3,815,560 Wahl et al discloses a surrounding resistive heater to maintain an electrolyte tube at high temperatures where its output voltage is least affected by temperature change. The aforementioned U.S. Ser. No. 787,900 Howarth discloses doping the solid electrolyte with iron oxide for temperature compensation. It additionally discloses disposing a resistance heater inside a solid electrolyte tube for maintaining the sensor at higher operating temperatures and for supplemental heating on start-up.

I have found a better way to include the heater in the sensor. For automotive applications particularly, the heated sensor should be rugged and reliable. In addition, the construction should be readily manufacturable for lower cost. Exposing the heater to the exhaust gas stream, around a solid electrolyte tube, can adversely affect both reliability of the heater and heating efficiency. Nesting the heater inside a closed end of a solid electrolyte tube, where it is isolated from the exhaust gas, has been previously proposed. However, such constructions use the inner surface of the tube for alignment and support, and involve complex mechanical and/or electrical arrangements. I believe that such constructions are unduly costly and raise questions of reliability and ruggedness.

I have found a new way to incorporate a heater in the sensor, that is particularly useful for automobile exhaust gas sensing. It involves initially forming a subassembly of a heater and a reference electrode terminal in which the heater is prealigned with respect to the solid electrolyte and isolated from the exhaust gas. The subassembly is simple, rugged, and reliable, yet readily mass produced. An elongated heater can readily be incorporated in a subassembly with the center terminal of an oxygen sensor such as disclosed in U.S. Pat. No. 3,844,920 Burgett et al. Such a heated sensor is rugged, efficiently heated, and yet readily manufacturable in high volume for lowest cost.

OBJECTS AND SUMMARY OF THE INVENTION

It is, therefore, an object of this invention to provide an improved heated solid electrolyte galvanic sensor.

A further object of this invention is to provide a solid electrolyte oxygen sensor having a heater supported on a tubular reference electrode as a subassembly in a fixed predetermined relationship, which subassembly is readily assemblable in predetermined relationship with the sensor solid electrolyte and a surrounding housing member.

Another object of this invention is to provide an improved method of making a heated solid electrolyte galvanic sensor.

These and other objects of the invention are attained in a solid electrolyte galvanic oxygen sensor having a heater supported on a tubular reference electrode in a desired predetermined concentric relationship with respect to the sensor electrolyte member. The heater and terminal comprise a subassembly readily assemblable with the electrolyte member and a surrounding metal housing. Means coacting with terminal and housing flanges hold the electrolyte member, heater-terminal subassembly and housing in a fixed predetermined concentric relationship.

BRIEF DESCRIPTION OF THE DRAWINGS

Other objects, features and advantages of the invention will become more apparent from the following description of the preferred embodiment thereof and from the drawings, in which:

FIG. 9 is an elevational view in partial section showing a third embodiment of this invention;

FIG. 10 is a sectional view along the line 10—10 of FIG. 9; and

FIG. 11 is a sectional view showing the heater-electrode terminal subassembly in the sensor embodiment shown in FIG. 9.

DESCRIPTION OF THE PREFERRED EMBODIMENTS

Figure 1:
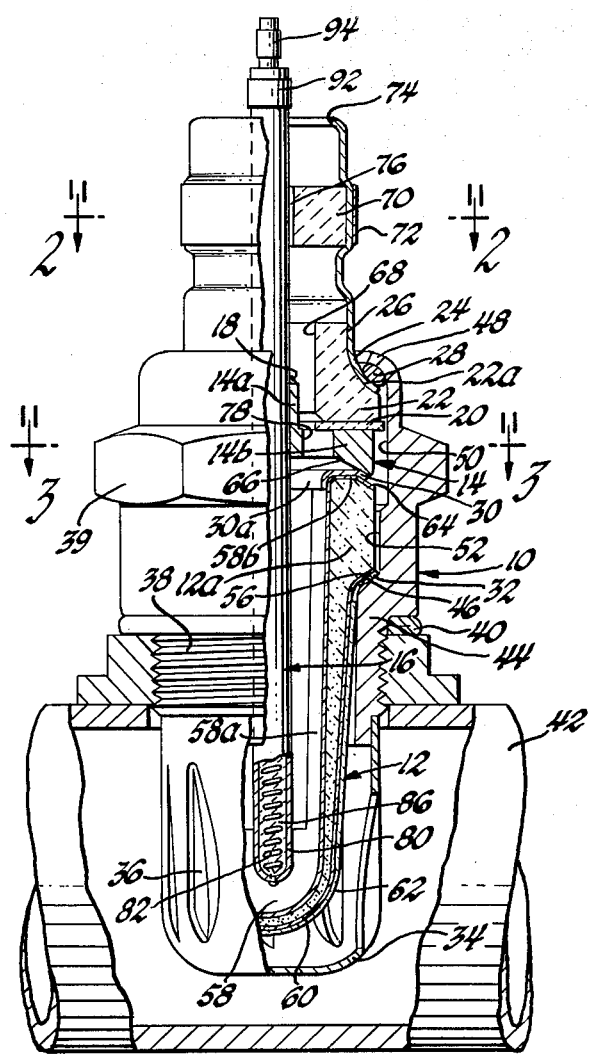
FIG. 1 is an elevational view in partial section showing one embodiment of an oxygen sensor made in accordance with this invention.
Figure 2:
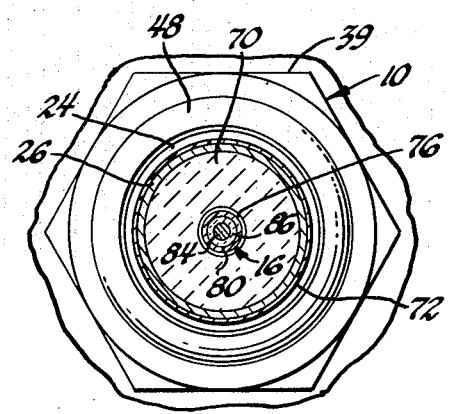
FIG. 2 is a sectional view along the line 2—2 of FIG. 1.
Figure 3:
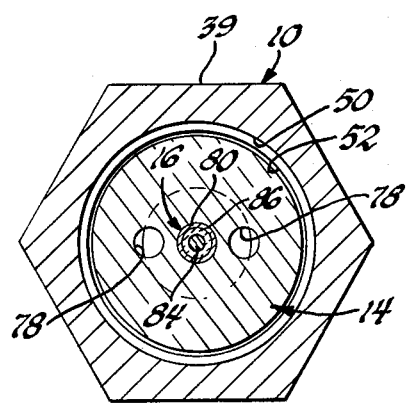
FIG. 3 is a sectional view along the line 3—3 of FIG. 1.
Figure 4:
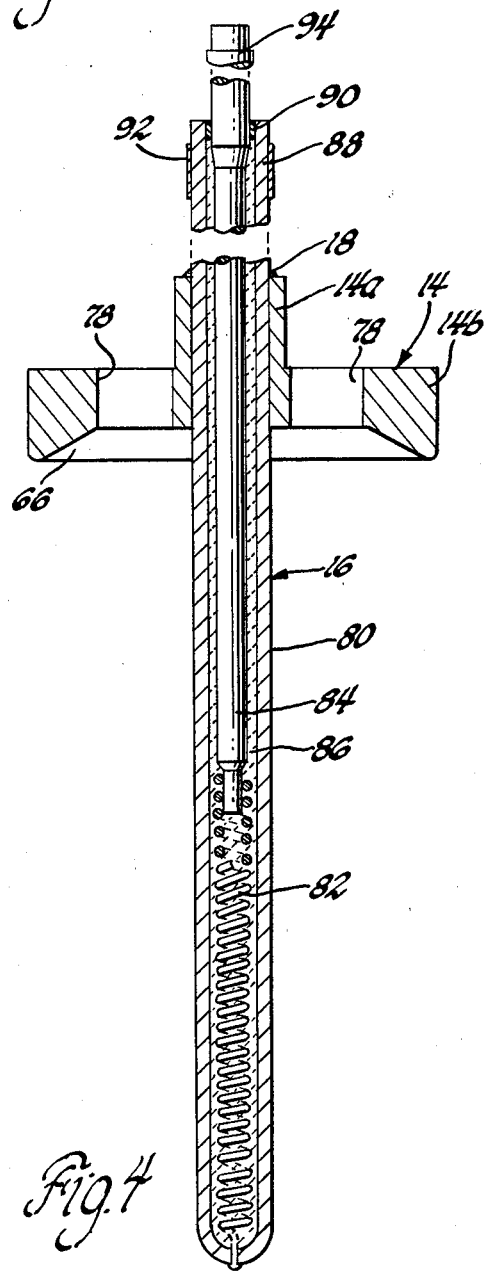
FIG. 4 is an enlarged view showing the heater-electrode terminal subassembly of the sensor shown in FIG. 1.
Figure 6:
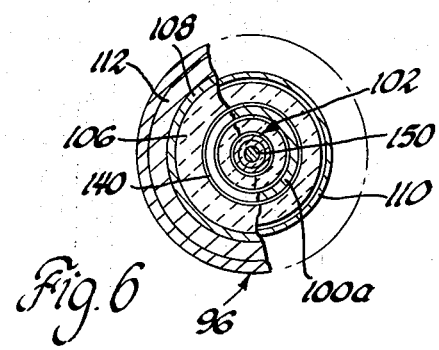
FIG. 6 is a sectional view along the line 6—6 of FIG. 5.
Figure 5:
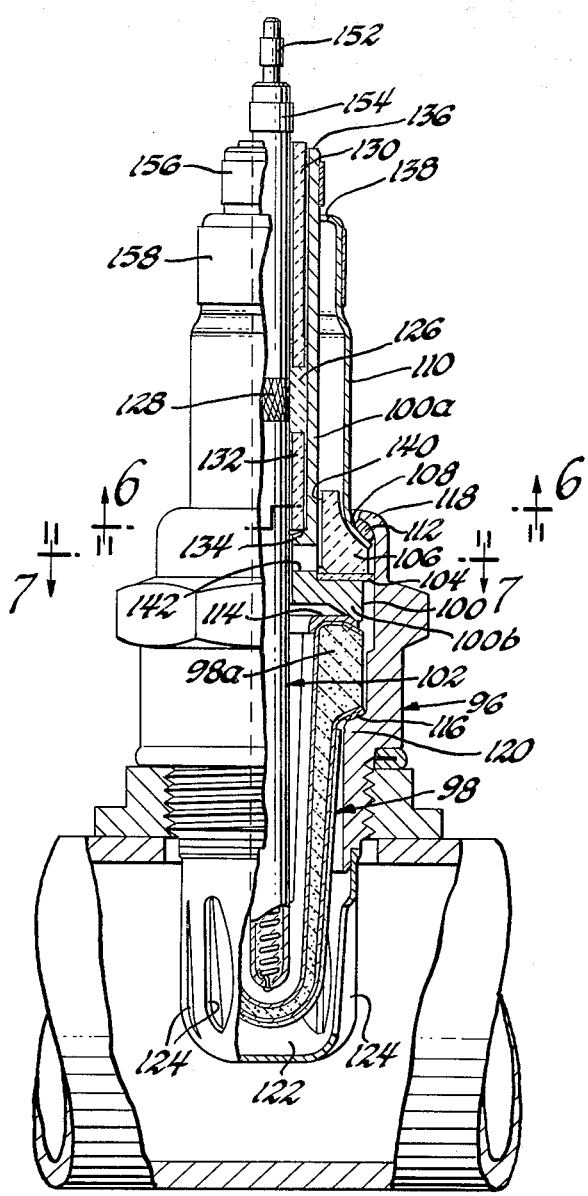
FIG. 5 is an elevational view in partial section showing a second embodiment of an oxygen sensor made in accordance with this invention.
Figure 7:
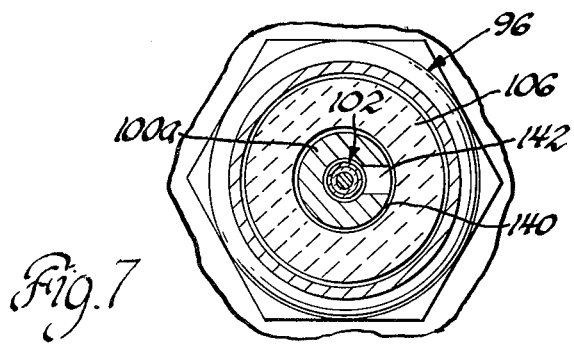
FIG. 7 is a sectional view along the line 7—7 of FIG. 5.
Figure 8:
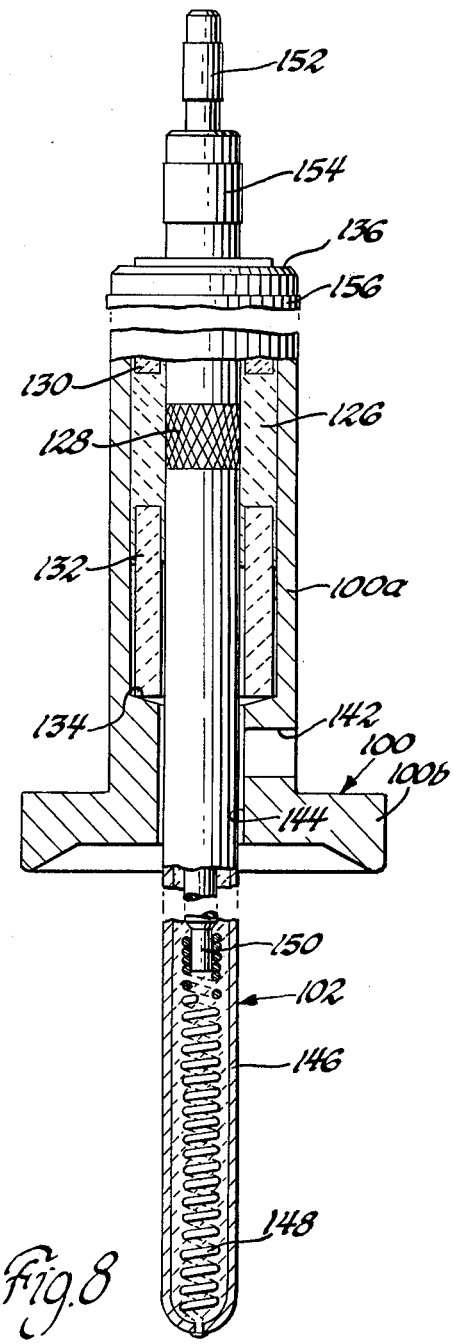
FIG. 8 is an enlarged view showing the heater-electrode terminal subassembly of the sensor shown in FIG. 5.

A first embodiment of this invention is shown in FIGS. 1-4. It includes a tubular metal shell 10, a solid electrolyte tube 12 that is closed at its bottom end, an electrode terminal member 14, and a heater 16. Electrode terminal member 14 has a central tubular portion 14a and a circumferential flange 14b at its lower end. Heater 16 is coaxial with terminal tube 14a and brazed to it at 18, whereby heater 16 and terminal 14 form a subassembly. FIG. 4 shows the subassembly.

Flat mica washer 20 is disposed on the upper surface of flange 14b. A ceramic ring 22 is concentrically disposed on mica washer 20 around terminal tube 14a. Ceramic ring 22 has an upward, decreasing taper 22a on its outer surface. A flared lower end 24 of a tubular, upper metal shield 26 nests on the tapered outer surface of ceramic ring 22. An annular metal gasket 28 surrounds the flared lower end 24 of shield 26. Below terminal flange 14b is an upper metal sealing ring 30, a circumferential flange 12a around the open upper end of the electrolyte tube 12, and metal lower sealing ring 32. A cup-shaped lower metal shield 34 is affixed to the lower end of shell 10, surrounding the otherwise exposed lower end of electrolyte tube 12. Lower metal shield 34 has louvers 36, for entry of exhaust gases. All of the aforementioned elements are coaxially aligned.

The sealing rings 28 and 30 can be of any soft metal, such as copper or nickel. The shell 10, metal shields 26 and 34, and at least the outer covering of heater 16 are made of metal which will withstand the conditions of sensor use, as for example at least stainless steel and preferably a nickel-based alloy. Ceramic ring 22 can be of any suitable ceramic, as for example alumina. Annular metal gasket 28 can be of soft steel.

On its outer surface, tubular metal shell 10 has circumferential threads 38 for mounting the sensor in an automobile exhaust pipe 42. Above threads 38 is an outer annular soft steel gasket 40. Above gasket 40 is a circumferential hexagonal array of surface flats 39 for tightening shell 10 in the exhaust pipe 42. If desired, the sensor could be alternatively mounted in an exhaust system manifold, tailpipe, or special parallel exhaust passage. On its inner surface, shell 10 has lower inward circumferential flange 44, providing an annular sloped shoulder 46. Shoulder 46 forms a tapered seat, on which lower sealing ring 32 is disposed. The upper end of shell 10 has an inward circumferential flange 48, formed by crimping or rolling over the soft steel gasket 28. Sloped shoulder 46 and upper flange 48 cooperate to concentrically clamp the aforementioned flanges, rings and washers within shell 10 in a predetermined fixed relationship.

The inner surface of shell 10 is generally cylindrical. Above shoulder 46 it has a larger diameter portion 50 and a smaller diameter portion 52. Portion 50 is of larger diameter to radially space shell 10 from the outer periphery of electrode terminal flange 14b, for electrical isolation purposes. Portion 52 is of a diameter only slightly larger than the outer diameter of the adjacent electrolyte tube flange 12a. The adjacent tube and shell diameters are sufficiently close to provide substantial coaxial alignment but not so close as to prevent easy assembly. About 0.040 inch or less nominal difference may be suitable.

Solid electrolyte tube 12 is tapered from its upper end to its closed lower end. The upper end has a larger diameter portion that forms a circumferential circular concentric flange 12a. Wall thickness on electrolyte tube 12 gradually decreases from flange 12a to the tube lower end. Flange 12a has a lower surface 56 which forms a sloped shoulder generally similar in slope to shoulder 46 of shell 10. Shoulder 46 and 56 cooperate, along with the shell reduced diameter portion 52, to coaxially align electrolyte tube 12 within shell 10. Lower metal sealing ring 32 between shoulders 46 and 56 provides a gas tight seal, and low resistance electrical communication between the surfaces.

A first porous thick film platinum electrode 58 fully covers the bottom inner surface of electrolyte tube 12. This inner electrode 58 serves as a reference electrode, in this case an air electrode for the sensor. A conductive strip-like coating 58a extends up the tube inner surface from electrode 58 to the open end of the tube 12, where it intersects with conductive coating 58b on the end face of electrolyte tube 12. Conductive coating 58b can merely be a stripe across the end face of electrolyte tube 12 or be a continuous circumferential coating. The platinum electrode 58 and conductive coatings 58a and 58b can be a continuous layer formed by brushing on a platinum paste and then firing it, as is usual.

A second porous thick film platinum electrode 60 covers the entire outer surface of tube 12, including the shoulder 56, below flange 12a. This outer electrode 60 serves as the exhaust gas electrode for the sensor. Outer platinum electrode 60 can be formed in the same manner as inner electrode 58. However, it may be more desirable to apply it by evaporation, sputtering or other such techniques. Outer electrode 60 is in low resistance electrical contact with shell 10 through the lower soft metal gasket 32. Hence, this electrode is also in low resistance electrical communication with upper shield 26 and exhaust pipe 42. A porous ceramic coating 62 of alumina, spinel or the like preferably covers the outer electrode 60 below electrolyte tube shoulder 56.

The upper end of electrolyte tube 12 is chamfered on its periphery, forming a sloped shoulder 64. The outer periphery of upper sealing ring 30 has a complementary contour. The inner periphery of sealing ring 30 has an axial flange 30a for concentric seating of sealing ring 30 on the open end face of tube 12. Inner electrode 58 and electrode terminal 14 are in low resistance electrical contact through platinum strip 58a, conductive coating 58b and sealing ring 30. Electrode terminal flange 14b has a sloped shoulder 66 on the outer periphery of its lower face, at least generally corresponding to sealing ring 30 and electrolyte tube shoulder 64. Sloped shoulders 64 and 66 cooperate to coaxially align electrode terminal 14 with electrolyte tube 12.

The upper surface of flange 14b is normal to the axis of terminal tube 14a. Also, the lower end face of ceramic ring 22 is normal to the longitudinal axis of coaxial passage 68 extending through the ceramic ring. The tapered outer surface 22a of ceramic ring 22 coacts with the adjacent metal gasket 28 and shell flange 48 to not only clamp the components together but also coaxially align ceramic ring 22 and its passage 68 within shell 10. As can be seen, the taper 22a on ceramic ring 22 is gradual at its upper end to enhance coaxial alignment and more abrupt at its lower end to enhance the clamping effect. The flared lower end 24 of upper metal shield 26 conforms to the taper 22a of the ceramic ring and nests thereon under gasket 28, whereby shield 26 is also coaxially aligned.

Upper shield 26 has an insulating annular spacer 70 around heater 16. Spacer 70 has an inner diameter slightly larger than the outer diameter of heater 16, to provide an air leakage path 76 therebetween. Spacer 70 is concentric with shield 26, which is concentric with shell 10. The upper end of shield 26 is open and radially spaced from heater 16. Shield 26 is therefore electrically isolated from heater 16. Shield 26 has a conformation to not only retain spacer 70 in place but also to retain a terminal connector (not shown) that may be attached. As mentioned, shield 26 is in low resistance electrical communication with outer electrode 60 on electrolyte tube 12. Shield 26 can therefore serve as a ground connection, if desired, instead of exhaust pipe 42. To insure lower resistance connection, an electroplated coating 72 of silver or the like can be provided on the upper end of shield 26.

The open upper end of shield 26 provides an aperture 74 through which ambient air can enter the interior of the sensor. Air entering the sensor through aperture 74 passes through leakage path 76 to an aperture 78 in terminal member flange 14b. From aperture 78, it passes into the interior of electrolyte tube 12, where it contacts inner electrode 58. To better show the air flow passages, the inner diameter of ceramic ring 22 is shown as considerably larger than the outer diameter of terminal tube 14a. However, this spacing can in fact be quite close, since only a very small rate of air flow is necessary during sensor operation. The rate of air flow resulting from air leakage due only to normal manufacturing tolerances, e.g. 0.003-0.005 inch minimum clearance, may be all that is necessary to provide an adequate air flow path. If so, the inner surface 68 of ceramic ring 22 also cooperates with terminal tube 14a, to further aid in coaxial alignment of the terminal member 14 and heater 16 with the various other components in the sensor assembly. To insure adequate air flow, a generous manufacturing tolerance may be desired, as for example a minimum spacing of 0.005-0.01 inch. Such a spacing will still enhance coaxial alignment. As can be understood from the foregoing description, all of the elements in the sensor assembly cooperate to permit ready assembly yet insure a high degree of coaxial alignment.

As specifically illustrated in FIG. 4, heater 16 is supported on electrode terminal 14 as a previously assembled subassembly. In the subassembly, a length of the outer surface of heater 16 is brazed to the inner surface of terminal tube 14a along their interface end at 18. Heater 16 and terminal 14 can easily be brazed under commercial production conditions while held in a jig where heater 16 is held coaxial with terminal tube 14a, and normal to the upper surface of electrode terminal flange 14b. Since heater 16 is in fixed coaxial alignment and longitudinal disposition with respect to terminal 14, it is inherently aligned with the balance of sensor components when terminal 14 is aligned. Since terminal 14 will align with electrolyte tube 12 upon assembly, heater 16 will also be aligned with and properly spaced from the electrolyte tube 12 upon assembly.

Heater 16 includes a tubular outer metal sheath 80 closed at its lower end within which a coaxial helical heating coil 82 is disposed. The lower end of coil 82 is welded to the bottom of sheath 80. The upper end of coil 82 is welded to a coaxial inner rod 84. Coil 82 and rod 84 are spaced from outer sheath 80 by ceramic insulation 86 as for example powdered magnesia. If desired, the open upper end 88 of sheath 80 can be closed by means of a sealing ring 90 of nonconductive material, as for example silicone rubber. The upper end 88 of sheath 80 has a silver coating at 92, as does heater rod 84, at 94, to insure low resistance electrical connections thereat. Heater 16 is therefore actuated by applying an electrical potential across sheath 80 and rod 84. If desired, heaters made in accordance with the teachings of U.S. Pat. No. 2,898,571 Moule et al, 3,252,122 Baxter can be used.

In this embodiment of the invention, both the heater 16 and inner electrode 58 share a common electrical terminal, which is the heater sheath 80 using the same terminal connector (not shown). Also, all terminals for the sensor are coaxial. Further, the heater electrode terminal subassembly can be ruggedly and simply constructed, using a minimal number of components and assembly steps to increase reliability. In addition, the subassembly can be accurately prealigned before assembly with the balance of sensor components. This heater-terminal subassembly is particularly useful for accelerating sensor warm-up. However, with appropriate electronic switching (not shown), it could also be used to keep the sensor at or above a predetermined operating temperature.

FIGS. 5-8 illustrate an embodiment of my heated sensor in which the heater is electrically isolated from both sensor electrodes and their respective terminals. In this embodiment of the invention heater 16 is mounted on the reference electrode terminal in a unique way. In addition, air flow to the reference electrode is uniquely baffled, to better isolate the reference electrode from contaminants. Otherwise, this sensor embodiment is essentially the same as hereinbefore described in connection with FIGS. 1-4.

The sensor of FIGS. 5-8 includes a metal shell 96, a solid electrolyte tube 98, an electrode terminal member 100 and a heater 102, all coaxially aligned, and with coaxial electrical terminal connection areas. The electrode terminal member 100 has a central tubular portion 100a and a circumferential flange 100b. Heater 102 is affixed to tubular portion 100a as will hereinafter be described. Above terminal flange 100b are successively a flat mica washer 104, a ceramic ring 106, a nested lower end flange 108 of an upper protective metal shield 110, and a soft steel metal gasket 112. Below flange 100b electrode terminal 100 is a soft metal sealing ring 114, a circumferential flange 98a on electrolyte tube 98, and a lower soft metal sealing ring 116. All of these components are compressed between an upper inward flange 118 and a lower inward flange 120 on shell 96. All of the foregoing components can be made of the same materials and serve the same function as described in connection with the preceding embodiment of the invention. Also, solid electrolyte tube 98 has inner and outer platinum coatings like tube 12 in FIGS. 1-3 for electrodes and conductor portions. Shell 96 further has a lower metal shield 122 with openings 124 therein to permit entry of exhaust pipe gases. In this embodiment of the invention the tubular portion 100a of electrode terminal member 100 has a greater extension than in the preceding embodiment of the invention. In addition, upper metal shield 110 does not include a spacer or a conformation to insure mechanical locking of a coaxial upper shield connector (not shown) that may be used.

Heater 102 is coaxially bonded within electrode terminal tubular portion 100a by fused glass 126. By fused glass, I mean a body of glass that has been melted and resolidified in place, whereby the resolidified glass body adheres to surfaces it contacts. The outer surface of heater 102 is knurled at 128 to enhance bonding of the fused glass 126. Above and below fused glass 126, heater 102 is respectively spaced from electrode terminal tubular portion 100a by an upper ceramic sleeve 130 and a lower ceramic sleeve 132. As can be seen, lower ceramic sleeve 132 is supported on a circumferential shoulder 134 on the inner surface of terminal tubular portion 100a. Ceramic sleeves 130 and 132 radially space heater 102 from the inner surface of electrode terminal tube 100b along its entire length. This not only physically spaces heater 102 and terminal tube 100b apart but electrically isolates them. Fused glass 126 initially was a cylindrical body slightly longer than the spacing between ceramic sleeves 130 and 132 shown in the drawing. The glass cylinder and sleeves 130 and 132 were assembled in tube 100a, with sleeve 130 projecting slightly beyond the end face 136 of terminal tubular portion 100a. Heater 102 was properly axially positioned within them. The glass cylinder was then melted and upper ceramic sleeve 130 moved inwardly into the position shown in the drawing. As a result, the molten glass completely filled an annular region between knurled portion 128 and the radially adjacent terminal tubular portion 100a. Concurrently, portions of the molten glass also were axially displaced a short distance along the inner and outer surfaces of the adjacent ends of the cermaic sleeves. Along this distance, the molten glass filled the space between the sleeves and the heater 102 and the tube 100a at least at the sleeve inner ends. The molten glass was then cooled, so that it solidified and bonded to heater 102, terminal tubular portion 100a, and ceramic sleeves 130 and 132. The glass also provides a seal. Its composition is not critical. Any glass can be used that melts at a temperature between the highest operating temperature expected for the device, and a temperature deleteriously affecting the heater or terminal materials such as their melting or sintering temperatures.

Tube 100a is normal to the upper surface 136 of flange 100b, as in the preceding embodiment of the invention. However, tube 100a is considerably longer. Hence, it can more accurately align heater 102 than terminal tube portion 14a of FIGS. 1-4 even when more liberal tolerances are used to ease assembly. Accordingly, ceramic sleeves 130 and 132 can be made somewhat loosely fitting within tube 100a to ease assembly. Nonetheless, they can effectively precisely align heater 102 within the tube. Generally the sleeves 130 and 132 should be only of the order of 0.1 mm smaller than tube 100a and bigger than heater 102. Even if somewhat loosely fitting, sleeves 130 and 132 are rigidly held in place by the fused glass 126 in the finished subassembly shown in FIG. 8. Thus, the axis of heater 102 is maintained substantially normal to the upper surface of electrode terminal flange 100b.

Air enters the sensor through an annular opening 138 in the upper end of shield 110. It passes down through shield 110 to an upper narrow generally annular passage 140 between ceramic ring 106 and electrode terminal tubular portion 100a. A clearance of approximately 0.005-0.01 inch between the outer diameter of tube 100a and the inner diameter of ceramic ring 106 provides the annular passage 140. Air entering annular passage 140 passes downwardly to aperture 142 in the lower wall of tube 100a, and through aperture 142 to a lower narrow generally annular passage 144 between heater 102 and the lower end of terminal tube 100b. A spacing of about 0.005-0.01 inch between the inner diameter of the tube 100b and the outer diameter of heater 102 provides the lower annular passage 144. Air passes through passage 144 into the interior of electrolyte tube 98, where it contacts the inner electrode. Thus, the interior of the electrolyte tube 98 communicates with outside air through a baffled passage, protecting it from particulate contaminants, water splash, etc. It should also be mentioned that passages 140 and 144 are formed by merely appropriately dimensioning the respective parts. Assembly is simple and no additional components or machining is required that adds to cost. In addition, the passages are so narrow as to merely constitute a generous manufacturing clearance, which still permits the inner surface of ceramic ring 106 parallel its axis to at least partially coast in coaxial alignment of electrode terminal 100.

As with tube 12 and upper shield 26 in the preceding embodiment of the invention, solid electrolyte tube 98 has an outer platinum coating which is in low resistance electrical communication with upper shield 110. Electrode terminal 100 is in low resistance electrical communication with a porous platinum electrode on the inner surface of electrolyte tube 98. Heater 102 is identical to heater 16 in the preceding embodiment of the invention. Thus, heater 102 includes an outer metal sheath 146 closed at its lower end that encloses a coaxial helical resistance heating element 148 and a coaxial metal rod 150. The lower end of the resistance heating element 148 is welded to the closed bottom end of sheath 146. The upper end of heating element 148 is welded to the lower end of metal rod 150. The heating element 148 and rod 150 are spaced from the surrounding metal sheath 146 by ceramic insulation, as for example powdered magnesia.

The heated sensor of FIGS. 5-8 thus has progressively larger silver plated terminal connections at 152, 154, 156 and 158. The innermost two terminal connections 152 and 154 are for applying a heating voltage across element 148. The outermost two terminal connections 156 and 158 are for obtaining an output voltage from platinum electrodes on the inner and outer faces of electrolyte tube 98.

The preceding embodiments of the invention hereinbefore described involve sensors having heater-electrode terminal tubular solid electrolyte members. It is also contemplated that heater-electrode terminal subassemblies of this invention can be used with disc-like solid electrolyte members such as illustrated in FIGS. 9-11. As with the preceding examples of the invention the sensor shown in FIGS. 9-11 includes an outer metal shell 160, a circular disc 162 of solid electrolyte material, an electrode terminal 164 having an outward circumferential flange 164a, and a heating element 166. Porous platinum electrodes 168 and 170 cover the upper and lower surfaces of electrolyte disc 162, respectively. Also, shell 160 has external conformations to facilitate mounting it in an exhaust pipe, and an inward upper flange 172 and an inward lower flange 176 for clamping sensor components together in a coaxial relationship.

Disposed on lower shoulder 178 is an outward circumferential flange 180 on a generally cup-shaped lower metal shield 82. Shield 182 has louvers 184 in its bottom end to permit exhaust gases to enter the shield and contact the lower platinum electrode 170. An annular soft metal sealing ring 186 is disposed on flange 180. Electrolyte disc 162 is circular and has an outer diameter less than the adjacent inner diameter of shell 160. Electrolyte disc 162 is disposed on sealing ring 186 with lower platinum electrode 170 contacting sealing ring 186. A second soft metal sealing ring 188 is disposed on the upper surface of electrolyte disc 162 and contacts the upper platinum electrode 168. Upper sealing ring 188 nests within a recess 190 in the lower end face of electrode terminal 164. Thus, terminal 164 is in low resistance communication with upper electrode 168, and shell 160 in similar communication with lower electrode 170.

The middle portion of electrode terminal 164 has an outward flange 164a. Flange 164a has an upper surface 192 that is normal to the longitudinal axis of terminal member 164. Successively disposed on flange upper surface 192 is a flat mica washer 194, a ceramic ring 196, a tubular upper metal shield 198 and an annular soft steel gasket 200. As in the preceding examples of this invention ceramic ring 196 has an upward taper 202 on its outer surface. The lower end 204 of upper shield 198 has a conforming flare and nests on the tapered upper part of ceramic ring 196. It is clamped against the outer periphery of the ceramic ring by the upper shell flange 172 through a soft steel ring 200.

Ceramic ring 196 has an inner coaxial cylindrical surface 206 of a diameter only slightly larger than the outer diameter of electrode terminal 164 above terminal flange 164a. A spacing of only about 0.1 mm can be used. This close fitting relationship further aids in maintaining terminal 164 coaxial with shell 160 when clamped between shell flanges 172 and 176. Such coaxial alignment prevents terminal 164 from contacting shell 160, to maintain them electrically isolated. However, if desired, an insulating sleeve (not shown) can be included in the assembly around terminal 164 within shell 160, axially disposed between terminal flange 164a and the upper surface of electrolyte disc 162. The insulating sleeve can thus cooperate with ceramic ring 196 in maintaining electrode terminal coaxial with and electrically isolated from shell 160.

It should also be mentioned that upper platinum electrode 168 does not completely extend to the edge of electrolyte disc 162. It only extends far enough across the upper face of disc 162 to make electrical contact with upper soft metal gasket 188.

As more clearly seen in FIG. 11, the heating element 166 and electrode terminal 164 of FIG. 9 are part of a preformed subassembly. Resistance heating element 166 is a planar coil, or spiral such as a heating element for an automobile cigar lighter. The outer end of the spiral element 166 is welded at 208 to the lower end of electrode terminal 164. The inner end of spiral element 166 is welded at 210 to the lower end of a coaxial heater terminal 212. Heating coil 166 forms a generally planar heater normal to the longitudinal axis of shell 160 and therefore parallel to the upper surface of disc 162. Terminal 164 thus forms a common terminal for both the heater element 166 and reference electrode 168, analogous to the embodiment shown in FIGS. 1-4.

Heater terminal 212 is coaxially affixed within tubular electrode terminal 164 by electrode terminal shoulders 214 and 216 which engage upper insulating ring 218 and lower insulating ring 220. Insulating rings 218 and 220 are respectively clamped against shoulders 214 and 216 by a spring clip 222 and a circumferential flange 224 on heater terminal 212. If desired, the upper ends of electrode terminal 164, upper shield 198 and heater terminal 212 can be silver plated (not shown) to insure a low resistance terminal connection.

The solid electrolyte members 12, 98 and 162 of the preceding embodiments of the invention can be of any suitable oxygen-ion-conductive ceramic, as for example stabilized zirconia, thoria or the like. Cubic zirconia stabilized with 8 mole percent yttria or 15 mole percent calcia can be used.

The embodiments of FIGS. 5-8 and 9-11 are considered to be improvements on the basic invention shown in FIGS. 1-4 and claimed herein. The FIG. 5-8 and 9-11 embodiments of this basic invention are separately described and specifically claimed in the concurrently filed United States patent applications Ser. No. 892,642 entitled "Solid Electrolyte Sensor with Electrically Isolated Heater" and Ser. No. 892,643 entitled "Heated Solid Electrolyte Oxygen Sensor", both of which are concurrently filed herewith in the names of M. P. Murphy et al and assigned to the assignee hereof.

The embodiments of the invention in which an exclusive property or privilege is claimed are defined as follows:

1. In a galvanic exhaust gas sensor having a solid electrolyte member, an outwardly flanged concentric tubular terminal for a reference electrode on one face of said electrolyte member, an inwardly flanged tubular metal shell surrounding said electrolyte member and said terminal, and means coacting with said terminal and shell flanges for biasing said member, terminal and shell together in a fixed predetermined relationship, the improvement wherein said tubular electrode terminal supports an electrical resistance element for heating said electrolyte member and at least one discrete resistance element terminal in a subassembly unitly assemblable with said electrolyte member and metal shell, said resistance element having a fixed predetermined axial alignment and displacement with respect to said electrode terminal, whereby said means for biasing the electrolyte member, electrode terminal and shell also aligns said resistance element with said electrolyte member and spaces said element and said electrolyte member a predetermined distance apart.

2. In a galvanic exhaust gas sensor having a circular solid electrolyte member, an outwardly flanged concentric tubular terminal for a reference electrode on a face of said electrolyte member, an inwardly flanged tubular metal shell surrounding said member and said terminal, and means coacting with said terminal and shell flanges for biasing said member, terminal and shell coaxially together in a fixed predetermined relationship, the improvement wherein said electrode terminal supports a resistance heating coil and at least one heating coil terminal in a subassembly that is unitly assemblable with said electrolyte member and said shell, said subassembly including a resistance heating coil, an elongated coil terminal axially extending through said tubular electrode terminal, means for supporting said coil terminal on said electrode terminal in fixed predetermined placement with respect to the longitudinal axis of said electrode terminal, and means for supporting said coil on said electrode terminal in a fixed predetermined placement with respect to said longitudinal axis with one end of said heating coil directly supported by said coil terminal, whereby said means for biasing the electrolyte member, electrode terminal and shell also aligns said heating coil with said electrolyte member and spaces it a predetermined distance from the electrolyte member face.

3. In a galvanic exhaust gas sensor having a circular solid electrolyte member, an outwardly flanged concentric tubular terminal for a reference electrode on an inner face of said member, an inwardly flanged tubular metal shell surrounding said member and said terminal, and means coacting with said terminal and shell flanges for biasing said member, terminal and shell coaxially together in a predetermined relationship, the improvement wherein said electrode terminal supports a resistance heating coil and at least one heating coil terminal in a mutually aligned coaxial subassembly having coaxial terminals, said subassembly including a resistance heating coil for heating said electrolyte member face, an elongated coil terminal extending through said tubular electrode terminal, means for coaxially supporting said coil terminal on said electrode terminal with ends thereof in a fixed predetermined displacement with respect to electrode terminal ends, means for coaxially supporting said coil on said electrode terminal in a fixed predetermined axial displacement with respect to said electrode terminal with one coil end directly affixed to said coil terminal and the other coil end in low resistance electrical contact with said electrode terminal, whereby said means for biasing the electrolyte member, electrode terminal and shell inherently also provides a coaxial heating coil uniformly spaced a predetermined distance from said electrolyte member inner face.

4. In a generally cylindrical galvanic exhaust gas sensor having a solid electrolyte tube with a closed end, an outwardly flanged concentric tubular terminal with an air passage for an air electrode on an inner face of said electrolyte tube, an inwardly flanged tubular metal shell surrounding said tube and said terminal, and means coacting with said terminal and shell flanges for biasing said tube, terminal and shell coaxially together in a fixed predetermined relationship, the improvement wherein said electrode terminal supports a resistance heating coil and two coil terminals in a mutually aligned coaxial subassembly having coaxial terminals, said subassembly including a tubular first coil terminal having a closed end for disposition within said electrolyte tube end, said first coil terminal coaxially affixed within and in predetermined placement along the longitudinal axis of said electrode terminal, a helical resistance heating coil coaxially supported by electrical insulation means within said coil terminal closed end and in electrical contact therewith at one end, a second coil terminal coaxially supported by electrical insulation means within the first coil terminal and in electrical contact with an opposite end of said coil, said first and second coil terminals presenting coil terminal connections coaxial with said electrode terminal at their ends opposite from said coil, whereby said means for biasing the electrolyte member, electrode terminal and shell inherently also provides a coaxial heating coil uniformly spaced a predetermined distance from the electrolyte tube inner face.

5. In a generally cylindrical galvanic exhaust gas sensor having a solid electrolyte tube flanged at one end and closed at the other, an outwardly flanged concentric tubular terminal with an air passage for an air electrode on the tube inner face, an inwardly flanged tubular metal shell surrounding said tube and said terminal, and means coacting with said terminal and shell flanges for biasing said tube, terminal and shell coaxially together in a fixed predetermined relationship, the improvement wherein said electrode terminal supports a coaxial non-electrically isolated resistance heater in a fixed prealigned subassembly unitly assemblable with said electrolyte tube and said shell, said subassembly including a tubular first heater terminal electrically contacting and coaxially affixed to said electrode terminal, closed and open opposite ends on said first heater terminal axially displaced outwardly from electrode terminal ends, a helical resistance heating element coaxially supported by electrical insulation means within said terminal closed end, said element having an axial dimension at least one-half the distance between said electrolyte tube closed end and its flange, one end of said heating element electrically contacting said closed end on said first terminal, a second heater terminal coaxially supported by electrical insulation means within the first heater terminal and electrically contacting the opposite end of said heating element, said first and second heater terminals having adjacent outer ends mutually axially displaced for coaxial connection of heater and electrode terminal leads.

6. In a method for assembling a heated galvanic exhaust gas sensor having a solid electrolyte member, an outwardly flanged concentric tubular terminal for a reference electrode on one face of said electrolyte member, an inwardly flanged tubular metal shell surrounding said electrolyte member and said terminal, and means coacting with said terminal and shell flanges for biasing said member, terminal and shell together in a fixed predetermined relationship, the improvement comprising the steps of affixing a resistance coil for heating said electrolyte member and at least one discrete resistance coil terminal to said electrode terminal to form a subassembly having a fixed predetermined relationship with respect to said electrolyte member and said shell, and assembling said subassembly with said electrolyte member and said shell wherein alignment of said electrode terminal also aligns said resistance coil with said electrolyte member in a predetermined spaced disposition.

* * * * *